US00PP33554P2

(12) United States Plant Patent
Van Swieten

(10) Patent No.: US PP33,554 P2
(45) Date of Patent: Oct. 12, 2021

(54) ***PHALAENOPSIS* ORCHID PLANT NAMED 'PHA1904894'**

(50) Latin Name: ***Phalaenopsis* hybrid**
Varietal Denomination: PHA1904894

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,235

(22) Filed: Apr. 21, 2021

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Jul. 10, 2021. p. 1.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHA1904894', particularly characterized by purplish-red flowers with dark red-purple lips, flowers with a flat shape in lateral view, weak curvature of the lateral lobes, short whiskers, short leaves, and is propagated by meristem tissue culture, is disclosed.

3 Drawing Sheets

Genus and species: *Phalaenopsis* hybrid.
Variety denomination: 'PHA1904894'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1904894'.

The new *Phalaenopsis* plant is a product of a planned breeding program conducted by the inventor in Bleiswijk, the Netherlands. The objective of this breeding program was to create a new *Phalaenopsis* plant with attractive, purplish-red flowers with dark red-purple lips, suitable for potted plant production.

The new *Phalaenopsis* plant 'PHA1904894' is a result of cross-pollination made by the inventor in May 2013 in Bleiswijk, the Netherlands, of the proprietary female, or seed parent, *Phalaenopsis* hybrid '01-3420' (unpatented) with the proprietary male, or pollen parent, *Phalaenopsis* hybrid '41754-06' (unpatented).

The new *Phalaenopsis* was selected by the inventor as a single plant within the progeny of the stated cross-pollination in a controlled greenhouse in Bleiswijk, the Netherlands, in March 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2289), by Applicant who obtained the subject matter disclosed directly from the inventor. 'PHA1904894' has not been made publicly available or sold anywhere in the world prior to the effective filing date of this application with the exception of sales or disclosures made one year or less before the effective filing date of this claimed invention by Applicant who obtained 'PHA1904894' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1904894' as a new and distinct variety of *Phalaenopsis* plant:

1) Purplish-red flowers with dark red-purple lips;
2) Flower shape in lateral view is flat;
3) Curvature of lateral lobe is weak;
4) Whiskers are short; and
5) Leaves are short.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in March 2021. Colors in the photographs may differ from the color values cited in the detailed botanical description, which accurately describe the actual colors of the new variety.

DESCRIPTION OF THE NEW VARIETY

Figure 1:
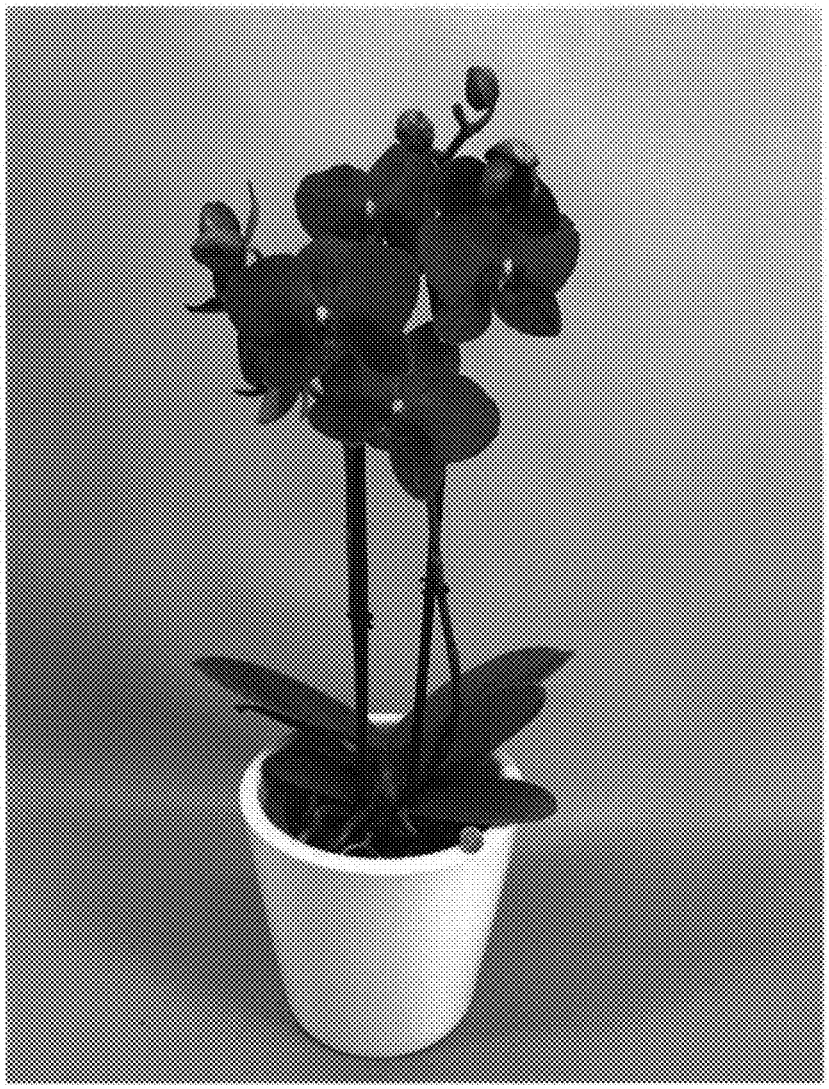
FIG. 1 shows the overall plant habit, including blooms, buds, and foliage of 'PHA1904894'.
Figure 2:
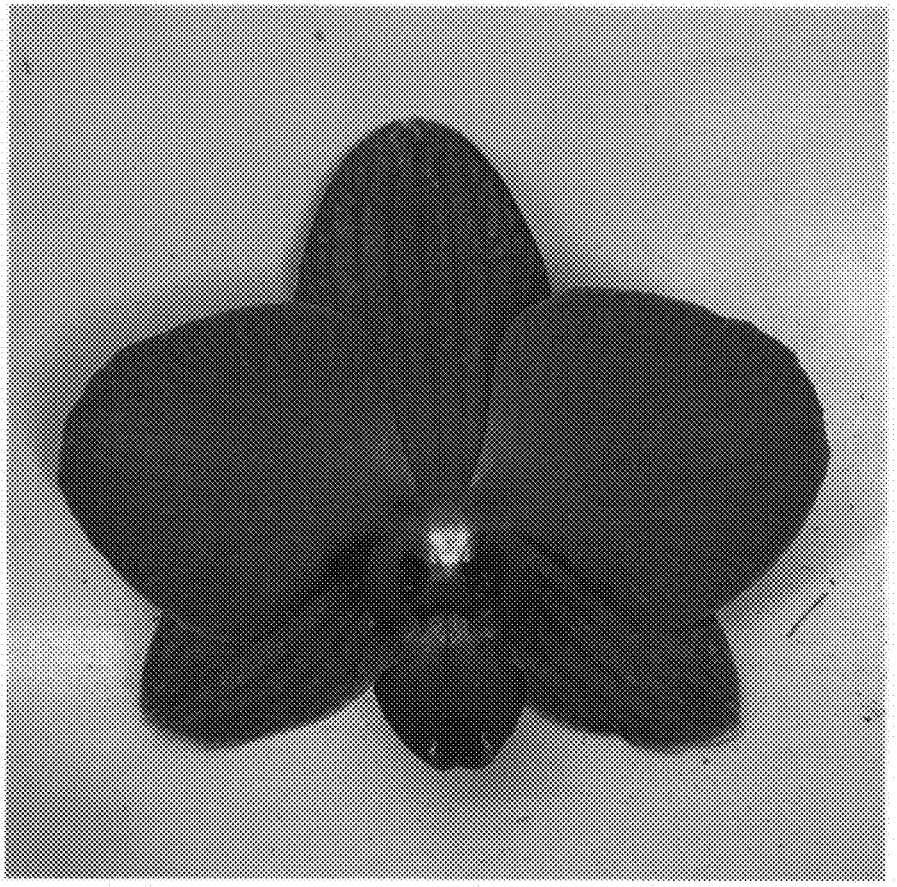
FIG. 2 shows a close-up of a flower of 'PHA1904894'.
Figure 3:
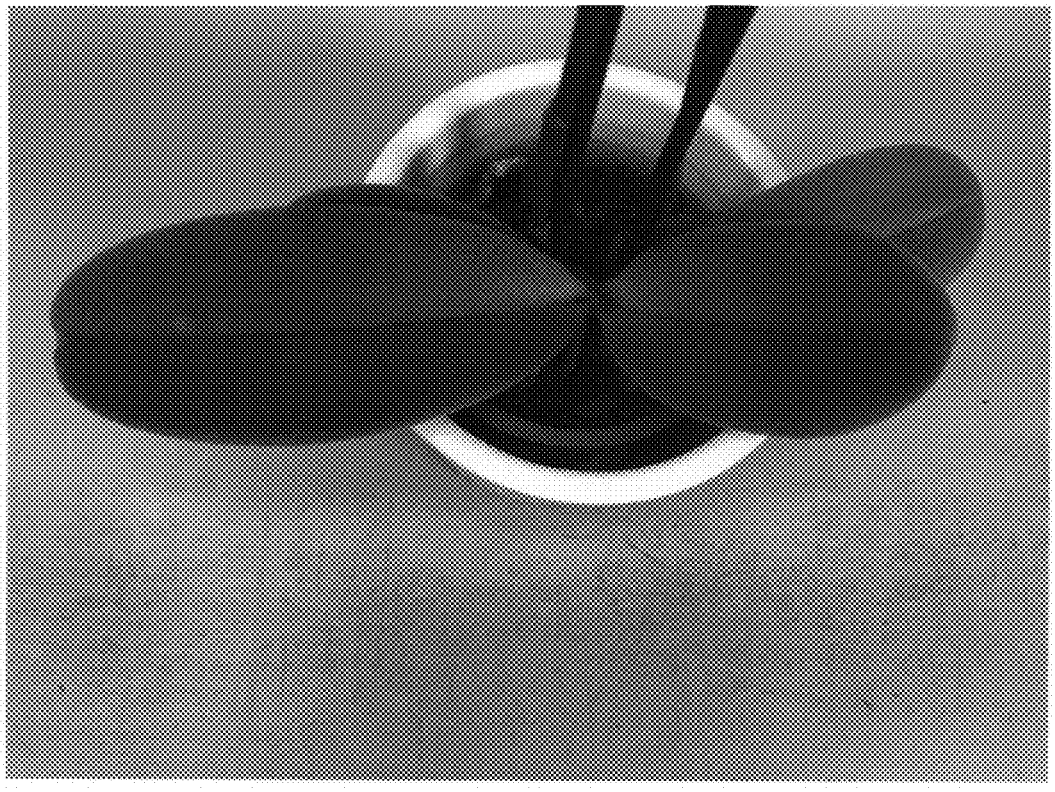
FIG. 3 shows an overhead view of the leaves of 'PHA1904894'.

The following detailed description sets forth the distinctive characteristics of 'PHA1904894'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA1904894'.

Parentage:

*Female parent*.—*Phalaenopsis* cultivar '01-3420' (unpatented).

*Male parent*.—*Phalaenopsis* cultivar '41754-06' (unpatented).

Propagation:

*Type*.—Meristem tissue culture.

Roots:

*Root description*.—Greyed-green (a color in between RHS 190B and RHS 190C) colored roots with branching lateral roots having greenish-yellow (RHS 145B) root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 33.0 cm to 38.0 cm.

*Width* (*measured from leaf tips*).—About 23.0 cm to 26.0 cm.

*Vigor*.—Strong.

Leaves:

*Mature leaves*.—Quantity per plant: 7 to 8 leaves are produced before flowering. Length (fully expanded): 11.0 cm to 14.0 cm. Width: 6.0 cm to 7.0 cm. Position of the broadest part of the leaf: At the middle. Shape: Oblong. Base shape: Moderately to slightly elongated. Apex: Almost rounded asymmetric. Leaf blade angle with the petiole (measured from the horizontal position): Between 10 degrees and 30 degrees. Leaf margin: Entire. Color: Upper surface: RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—5 to 7.

*Length*.—33.0 cm to 38.0 cm.

*Diameter*.—4.0 mm to 5.0 mm.

*Strength*.—Strong.

*Aspect*.—Upright to slightly pendent.

*Texture*.—Smooth.

*Color*.—Mix of brown (RHS 200C) and yellow-green (RHS 146D).

*Internode length*.—3.0 cm to 4.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 90.0 mm to 120.0 mm.

*Flowering time*.—First flowers can be expected 10 to 11 months after planting in a 12-cm pot.

*Flower*.—Height: 72.0 mm to 77.0 mm. Diameter: 83.0 mm to 88.0 mm. Depth of lip: 21.0 mm to 23.0 mm.

Flower longevity.—On the plant: 12 to 14 weeks.

*Flower shape*.—Flat.

*Fragrance*.—Absent.

*Flower bud*.—Average size: Medium to large. Length: 21.0 mm to 23.0 mm. Width: 17.0 mm to 19.0 mm. Shape: Egg shaped. Color: Yellowish-green (RHS N144A) with a touch of dark purplish-red (a color in between RHS N79B and RHS N79C); dark purplish-red stripes (RHS N79B).

*Petals*.—Arrangement: Open/free. Shape: Semi-circular. Apex: Rounded asymmetric. Margin: Weakly undulated. Length (from base to tip): 39.0 mm to 41.0 mm. Width: 41.0 mm to 43.0 mm. Position of the broadest part of the petal: Toward the base. Color (when fully opened): Upper surface: Basic color: Purplish-red (RHS 61A). Over color: Dark purplish-red stripes (RHS N79C). Lower surface: Basic color: Purplish-red (RHS 70A). Over color: Light yellow-green (RHS 145C); diluting purplish-red stripes (RHS 64A). Number of spots and stripes on the petals (upper surface): Many stripes. Color of spots and stripes on the petals (upper surface): RHS N79C. Density of netting of the petals (upper surface): None. Color of the netting (upper surface): Not applicable.

*Dorsal sepal*.—Shape: Elliptic. Apex: Obtuse to slightly emarginated symmetric. Margin: Entire. Length (from base to tip): 45.0 mm to 47.0 mm. Width: 31.0 mm to 33 0 mm. Position of the broadest part of the dorsal sepals: At the middle. Color (when fully opened): Upper surface: Basic color: Purplish-red (RHS 61A). Over color: Dark red stripes (RHS 59A) and dark purplish-red netting (RHS N79C). Lower surface: Basic color: Yellow-green (a color in between RHS N144A and RHS 145C). Over color: Purplish-red toward margins and stripes (RHS 71A). Number of spots and stripes on the dorsal sepals (upper surface): Medium stripes. Color of spots and stripes on the dorsal sepals (upper surface): RHS 59A. Density of netting of the dorsal sepals (upper surface): Low. Color of the netting: RHS N79C.

*Lateral sepals*.—Shape: Ovate. Apex: Obtuse asymmetric. Margin: Weakly undulated. Length (from base to tip): 40.0 mm to 42.0 mm. Width: 26.0 mm to 28.0 mm. Position of the broadest part of the lateral sepals: Toward the base. Color (when fully opened): Upper surface: Basic color: Purplish-red (RHS 61A). Over color: Touch of light yellow-green (RHS 145C) and dotted (RHS 59A) at the base; purplish-red shade (RHS 59B) on one side; stripes and netting (a mix of RHS 59A and RHS N79C). Lower surface: Basic color: Yellow-green (a color in between RHS N144A and RHS 145C). Over color: Purplish-red (RHS 59B) toward margins and purplish-red stripes (RHS 70A). Number of spots, dots, and stripes on the lateral sepals (upper surface): Medium dots at base; medium stripes. Color of spots, dots, and stripes on the lateral sepals (upper surface): Dots (RHS 59A); stripes (a mix of RHS 59A and RHS N79C). Density of netting of the lateral sepals (upper surface): Medium. Color of the netting (upper surface): A mix of RHS 59A and RHS N79C.

*Labellum* (*lip*).—Whiskers: Present. Length of whiskers: 3.0 mm to 4.0 mm. Color of whiskers: Dark red-purple (a color in between RHS N78A and RHS N79C) with white tips (RHS NN155C). Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Weakly undulated. Length: 15.0 mm to 17.0 mm. Width: 6.0 mm to 8.0 mm. Color: Upper surface: Touch of light greenish-yellow (a mix of RHS 8B and RHS 8C) at the base; dark red spots (RHS 59A); dark red-purple (a color in between RHS N78A and RHS N79C) toward the tip. Lower surface: Light yellow-green (RHS 196C) and touch of red (RHS 181B) at the margin on one side toward base; dark red (RHS 59A) and reddish-purple (RHS N78A) toward the tip. Number of spots and stripes on the lateral lobe: Few spots. Color of spots and stripes on the lateral lobe: RHS 59A. Density of netting of the lateral lobe: None. Color of the netting: Not applicable.

*Apical lobe*.—Shape: Trullate. Margin: Entire. Length: 20.0 mm to 22.0 mm. Width: 17.0 mm to 19.0 mm. Color: Upper surface: Touch of red (RHS 185B) at the base; dark red margins (RHS 59A) at wings and dark red-purple (a color in between RHS N78A and RHS N79C) toward whiskers. Lower surface: Light greenish-yellow (RHS 160C) at the base; dark red margins (RHS 59A) at wings; purplish-red (RHS 64A) and dark red-purple (a color in between RHS N78A and RHS N79C) at the middle with a white region (RHS NN155C) toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small to medium. Height: 5.0 mm to 6.0 mm. Length: 3.0 mm to 4.0 mm. Width: 3.0 mm to 4.0 mm. Color: Light yellow-green (RHS 4D) on sides; greenish-yellow tips (RHS 6A) and purplish-red stripes (RHS 59B).

Reproductive organs:

*Column*.—Length: 8.0 mm to 10.0 mm. Diameter: 4.8 mm to 5.3 mm. Color: Reddish-purple (RHS N78A).

*Pollinia*.—Quantity: 2. Diameter: 0.9 mm to 1.1 mm. Color: Yellow-orange (RHS 23A).

*Ovary*.—Length: 10.0 mm to 12.0 mm. Diameter: 3.0 mm to 3.4 mm.

*Pedicel*.—Length: 36.0 mm to 38.0 mm. Diameter: 3.5 mm to 3.9 mm. Color: Yellow-green (RHS 146C) with a hint of brown (RHS N199B) at the base; light yellow-green (RHS 145C) toward flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1904894' differs from the female parent plant '01-3420' (unpatented) in that 'PHA1904894' has smaller flowers than '01-3420'.

'PHA1904894' differs from the male parent plant '41754-06' (unpatented) in that 'PHA1904894' has flowers with main color of purplish-red and whiskers, whereas '41754-06' has flowers with a main color of red and no whiskers. Additionally, 'PHA1904894' has larger flowers than '41754-06'.

'PHA1904894' is most similar to the commercial *Phalaenopsis* plants named 'PHALJAKYJE' (U.S. Plant patent application Ser. No. 16/974,383) and 'PHALAPEK' (unpatented). 'PHA1904894' differs from the commercial variety 'PHALJAKYJE' in that 'PHA1904894' has lateral lobes that are spotted at the base, flowers with a flat shape in lateral view, and raceme inflorescence, whereas 'PHALJAKYJE' has lateral lobes that are striped at the base, flowers with a slightly concave shape in lateral view, and panicle inflorescence. Additionally, 'PHA1904894' has shorter leaves than 'PHALJAKYJE'.

'PHA1904894' differs from the commercial variety 'PHALAPEK' in that 'PHA1904894' has trullate apical lobes, dark red-purple whiskers with white tips, and flowers with a flat shape in lateral view, whereas 'PHALAPEK' has rhombic apical lobes, dark red whiskers, and flowers with a concave shape in lateral view. Additionally, 'PHA1904894' has shorter leaves than 'PHALAPEK'.

I claim:

1. A new and distinct variety of *Phalaenopsis* plant named 'PHA1904894', substantially as described and illustrated herein.

* * * * *